United States Patent [19]

Leighton et al.

[11] Patent Number: 4,996,045
[45] Date of Patent: Feb. 26, 1991

[54] HAIR FIXATIVE COMPOSITIONS CONTAINING ALPHA-AMINOMETHYLENE PHOSPHONATE BETAINES

[75] Inventors: John Leighton, Flanders; Carmine Iovine, Bridgewater, both of N.J.

[73] Assignee: National Starch and Chemical Investment Holding Corporation, Wilmington, Del.

[21] Appl. No.: 272,572

[22] Filed: Nov. 16, 1988

[51] Int. Cl.$^5$ .............................. A61K 7/06; A61K 7/11
[52] U.S. Cl. ........................................ 424/70; 424/47; 424/71; 424/78; 424/DIG. 1; 424/DIG. 2
[58] Field of Search ............... 424/70, 71, 47, 78, 424/DIG. 1, DIG. 2

[56] References Cited

U.S. PATENT DOCUMENTS

| | | | |
|---|---|---|---|
| 3,836,537 | 9/1974 | Boerwinkle | 424/71 |
| 3,927,199 | 12/1975 | Micchelli et al. | 424/47 |
| 3,996,146 | 12/1976 | Tarasov et al. | 252/142 |
| 4,075,131 | 2/1978 | Sterling | 424/78 |
| 4,166,845 | 9/1979 | Hansen et al. | 424/78 |
| 4,247,538 | 1/1981 | Barker | 424/70 |
| 4,358,567 | 11/1982 | Haymann et al. | 525/359.4 |
| 4,402,977 | 9/1983 | Grollier et al. | 424/70 |
| 4,507,280 | 3/1985 | Pohl et al. | 424/70 |
| 4,526,781 | 7/1985 | Goldberg | 424/47 |
| 4,707,306 | 11/1987 | Leighton et al. | 260/501.12 |
| 4,778,865 | 10/1988 | Leighton et al. | 526/240 |

*Primary Examiner*—Merrell C. Cashion, Jr.
*Assistant Examiner*—Amy Hulina
*Attorney, Agent, or Firm*—Ellen T. Dec; Edwin M. Szala

[57] ABSTRACT

Improved hair fixative compositions are prepared from copolymers containing specific alpha-aminoethylenephosphonate betaine monomers. The resulting fixative compositions exhibit an enhanced tolerance of non-halogenated hydrocarbons, yet also exhibit a high degree of shampoo removability, making them particularly useful in aerosol formulations using non-halogenated hydrocarbon propellants.

14 Claims, No Drawings

HAIR FIXATIVE COMPOSITIONS CONTAINING ALPHA-AMINOMETHYLENE PHOSPHONATE BETAINES

BACKGROUND OF THE INVENTION

This invention relates to improved hair fixative compositions containing specific alpha-aminomethylene phosphonate betaine copolymers.

These resultant hair fixative compositions exhibit superior hydrocarbon tolerance, and are thus suitable for use in aerosol applications wherein hydrocarbon propellants are used, and where easy removability from the hair by shampooing is desired.

In order to be effective in aerosol hair spray formulations, the film forming, polymeric binders utilized therein as well as the films derived therefrom must meet a rigid set of requirements. The binders used in such formulations should be soluble in organic solvents and completely compatible with the propellants and solvents ordinarily employed in the aerosols; yet the films cast on the hair from such formulations should, ordinarily, be either water soluble or water dispersible in order to facilitate their easy removal from the user's hair by shampooing. As is readily visualized, this is an unusual combination of properties which is further complicated by the requirement that the binder used in such formulations be stable in the presence of, an unreactive with, the perfumes or other optional ingredients utilized in hair spray formulations.

Further, the films cast from the solutions of these binders should be flexible and yet they should have sufficient strength and elasticity to hold the hair; they should adhere well to hair so as to avoid dusting or flaking off when the hair is subjected to varying stresses; they should readily allow the hair to be re-combed; they should maintain a nontacky state despite varying environmental conditions; they should be clear, transparent and glossy and should maintain this clarity on aging; they should possess good anti-static properties; and, as previously noted, they should be easily removable by the use of water and/or soap or shampoo.

Many polymeric systems have been utilized in an attempt to meet these stringent requirements. Among these are included polyvinylpyrrolidone copolymers, and N-vinyl pyrrolidone with vinylacetate, 5-5'dimethyl hydantoinformaldehyde resins and copolymers of methyl vinyl ethers and maleic acid half esters, etc. Though each of the latter systems has met at least some of the above cited requirements, none has exhibited all of these requirements to an optimum degree.

For example, carboxylated vinyl polymeric hair spray resins, particularly the carboxylated acrylate, and/or acetate based resins, have long been favored for use in aerosol hair spray formulations. Also useful are a class of carboxylated ester polymers comprising an acrylamide, an acidic film forming comonomer, and at least one polymerizable comonomer which are described in U.S. Pat. No. 3,927,199. In order to obtain optimum benefits for the use of such acidic resins, it has been required to neutralize at least a portion, and preferably most or all, of the available carboxyl functionalities with specific alkaline reagents, e.g., amines and aminohydroxy compounds, as described in, for example, U.S. Pat. Nos. 2,996,471; 3,405,084; 3,577,517; etc. Thus, alkaline reagents which are suggested for such neutralizations include ammonia, lithium hydroxide, potassium hydroxide, sodium hydroxide, mono-, di- or triethanolamine, mono-, di or tripropanolamine, morpholine, amino methyl propanol, amino methyl propanediol, hydroxy ethyl morpholine, and mixtures thereof. The purpose of this neutralization step is both to improve the water solubility or dispersibility of the resin thus permitting easy removal from the hair by merely washing with shampoo and also to affect the degree of flexibility of the resultant film when sprayed on the hair (i.e., to produce a soft film, normal film or a film suitable for "hard to hold" hair). Additionally, U.S. Pat. No. 4,192,861 teaches the use of long chain amines for the neutralization of specific polymers in aerosol hairspray systems.

One class of neutralizing agent which has been extensively used in the hair spray industry is the amines, especially 2-amino-2-methyl-1-propanol (AMP) and 2-amino-2-methyl-1,3-propanediol (AMPD). These agents are quite versatile in their utility and are used in a number of formulations marketed by a number of manufacturers.

Until recently, the majority of aerosol formulations employed halogenated hydrocarbons, particularly the chlorofluorocarbons as propellants. Such propellants were uniquely suitable for use in aerosol systems since they were compatible with polar solvents, including water. The resins employed can also have high solubility in these solvents and, thus, can be easily removed from the hair by shampooing.

Recent ecological concerns, however, have resulted in a shift away from the use of halogenated hydrocarbon propellants and cosolvents and toward the use of hydrocarbons as propellants in aerosol hair spray formulations. In such systems, the binder and any optional ingredients are dissolved in a suitable solvent, such as an alcohol, and the hydrocarbon serves as the propellant. Unfortunately, the use of these propellants produces a number of problems, some of which are due to the decrease in solubility of the binder in the solvent system as the hydrocarbon content is increased. Thus, while the carboxylated resins are soluble in the anhydrous alcohol halocarbon systems of the prior art, and are the commercially preferred resins for their holding properties, their reduced solubility in the alcohol-hydrocarbon propellant may render them unacceptable to the industry for use in aerosol systems containing high levels of hydrocarbon propellants.

A number of hydrocarbon tolerant carboxylated resins have, thus, been developed for use with hydrocarbon propellants. The development, however, presents a double-edged sword, for once the systems become sufficiently tolerant of the non-polar propellant, they ordinarily become extremely resistant to water dispersion and thus, to the removal from hair by shampooing. While this resistance to shampoo removal has been observed, to a greater or lesser extent, with all hydrocarbon tolerant carboxylated resins, some resins have been developed which lessen the problem.

One acrylate-based resin marketed by National Starch and Chemical Corporation exhibits exceptionally high hydrocarbon tolerance. The resin, a terpolymer comprising 30% (by weight) N-t-octylacrylamide, 51% isobutylmethacrylate, and 19% acrylic acid, has enjoyed wide acceptance by the industry. When neutralized by an appropriate neutralizing agent, the resin is tolerant to a high concentration of hydrocarbon and exhibits an acceptable level of shampoo removability. However, complete removal of the film from the hair can require repeated washes, making it unattractive in some applications.

Thus, there exists a need for hair spray formulations which exhibit acceptable shampoo removability as well as high tolerance of hydrocarbon propellants which are becoming increasingly important in the industry.

SUMMARY OF THE INVENTION

In accordance with the present invention, hair fixatives are prepared comprising an appropriate carrier together with a functional amount of an alpha-aminomethylene phosphonate betaine copolymer. In particular, the invention relates to the use copolymers prepared from betaine monomers having the general formula:

$$\underset{CH_2}{\overset{R^1}{\underset{\|}{C}}}\diagup^X\diagdown (CH_2)_a - \overset{R^2}{\underset{R_3}{N^+}} - CH_2 - \overset{Y}{\underset{|}{CH}} - (CH_2)_b - N\diagup^Z\diagdown_{CH_2 - P\diagup^{O-}_{\diagdown OM}}^{\diagup}\quad (I)$$

$R^1$ is hydrogen or methyl;

X is $$\overset{O}{\underset{\|}{C}} - O, \overset{O}{\underset{\|}{C}} - NH, \text{ or } CH_2;$$

a is 0, 1, 2, or 3, with the condition that when X is $$\overset{O}{\underset{\|}{C}} - O \text{ or } \overset{O}{\underset{\|}{C}} - NH,$$

that a be greater than 1;

$R^2$ and $R^3$ are independently $C_1$–$C_6$ alkyl, aryl, benzyl, or cyclohexyl;

Y is hydrogen or hydroxyl;

b is 0, 1, 2, or 3;

Z is $C_1$–$C_6$ alkyl, aryl, benzyl, cyclohexyl, or $$CH_2 - P\overset{O}{\underset{\diagdown OM}{\diagup}}^{OM};$$

M is hydrogen, metallic cation, or ammonium ion.

These compositions, are generally prepared in a sufficiently neutralized form and, as such do not require further neutralization although in some instances it may be desirable to do so. The compositions exhibit a high tolerance to hydrocarbons, yet the films cast on the hair by such resins are easily removable by shampooing. Thus, the compositions are especially useful in aerosol formulations utilizing hydrocarbon propellants.

Useful herein are copolymers of the betaine prepared with any ethylenically unsaturated copolymerizable comonomer. These betaine copolymers are described in U.S. Pat. Nos. 4,707,306 and 4,778,865 issued to applicants on Nov. 17, 1987 and Oct. 18, 1988, respectively, the disclosures of which are incorporated herein.

The neutralized copolymers, when subsequently employed in an aerosol system, will tolerate high levels of hydrocarbon propellant in the aerosol system, yet maintain a high degree of shampoo removability. Advantageously, this permits a much higher level of copolymer to be present in the aerosol formulation. In addition, the compositions exhibit superior hair-holding properties and, when applied as an aerosol to the hair, produce a hard but flexible film which displays excellent subjective properties such as high gloss, good static resistance, and superior adhesion to hair.

DETAILED DESCRIPTION OF THE PREFERRED EMBODIMENTS

Thus, the monomeric betaines used in the hair care formulation are prepared by the reaction of a compound of the general structure $$\underset{CH_2}{\overset{R^1}{\underset{\|}{C}}}\diagup^X\diagdown (CH_2)_a - N\diagup^{R^2}\diagdown_{R^3}\quad (II)$$

where $R^1$, X, a, $R^2$, and $R^3$ are as defined above with compounds of the following general structures:

$$L - CH_2 - \overset{Y}{\underset{|}{CH}} - (CH_2)_b - N\diagup^Z\diagdown_{CH_2 - P\diagup^{OM}_{\diagdown OM}}^{\diagup}\quad (III)$$

or $$\underset{CH_2}{\overset{O}{\diagdown}}CH - (CH_2)_b - N\diagup^Z\diagdown_{CH_2 - P\diagup^{OM}_{\diagdown OM}}^{\diagup}\quad (IV)$$

where L is halogen or $$O - \overset{O}{\underset{\overset{\|}{O}}{\overset{\|}{S}}} - R^4$$

with $R^4$ being alkyl or aryl; and Y, b, Z, and M are as defined above.

The choice of the particular functional groups Y and Z in the betaine will vary depending upon the desired solvent used in the hair fixative formulation. Thus, in cases where ethanol or other alcohols are employed, Y is preferably hydrogen and Z is preferably $C_1$–$C_6$ alkyl, aryl, benzyl or cyclohexyl. If water is used as the solvent it is also possible to use a betaine where Y is hydroxyl and Z is phosphonomethyl.

The reaction of these compounds is carried out in a suitable solvent (usually water or alcohol/water or alcohol) at a pH of 7–9 and a temperature of 10°–90° C. Under such conditions the reaction is substantially complete in one-half to ten hours, preferably one to five hours. The solution may be acidified with mineral acid if the acid form of the monomer, (where M is hydrogen), is desired.

If bisphosphonomethyl chloroethylamine is used as the compound of Formula III, the reaction is carried out at a pH of about 7–9 obtained by the addition of sodium hydroxide, preferably pH 8, and a temperature of 20°–60° C., preferably about 50° C. This reaction is carried out under atmospheric pressures and is substantially completed within a period of about 3 hours. Using this starting material, the resulting betaine will correspond to formula I where y is H, Z is —CH$_2$—PO(ONa)$_2$ and b is 0.

In order to produce compounds of formula I where Y is OH, b is 1 or 2, and Z is —CH$_2$—PO(OH)$_2$, chlorohydroxypropyl (or butyl) bisphosphonomethylamine is used as the compound of Formula III and the reaction is carried out at a pH of about 6 to 8, preferably about pH 7, using the same temperature and other conditions described previously. The resulting betaine monomers are copolymerized with up to 95% by weight, preferably at least 50%, most preferably more than 80% by weight of an ethylenically unsaturated comonomer or mixture of comonomers.

Representative comonomers include acrylic or methacrylic acids and esters thereof with C$_1$–C$_{18}$ alcohols; unsaturated carboxylic acids such as itaconic and maleic acids and esters thereof, (meth)acrylamide and their N-substituted derivatives, such as N-mono and N-dimethyl, -ethyl, -propyl, and -butyl acrylamide or methacrylamide and N-mono or diphenylacrylamide; vinyl esters such as vinyl acetate or vinyl propionate; vinyl ethers such as butyl vinyl ether; N-vinyl lactams such as N-vinyl pyrrolidinone; halogenated vinyl compounds such as vinyl chloride and vinylidene chloride or fluoride; alkyl vinyl ketones such as methyl or ethyl vinyl ketone; diesters such as dimethyl, diethyl, dipropyl, dibutyl, diphenyl, dibenzyl, and di(phenylethyl) itaconate, maleate, and fumarate; and polyethyleneglycol acrylate or methacrylate or polypropyleneglycol acrylate or methacrylate.

In addition to the comonomers described above, the copolymers can also contain up to about 20% of one or more optional comonomers. These monomers, if present are generally used in amounts of at least 2.5% and can be included to tailor and/or enhance certain properties of the copolymer such as hair adherance, hardness, flexibility, antistatic properties and the like. Among these comonomers are hydroxyalkyl esters of acrylic and methacrylic acids such as hydroxypropyl acrylate and methacrylate, hydroxybutyl acrylate and methacrylate, hydroxystearyl acrylate and methacrylate and hydroxyethyl acrylate and melthacrylate; alkyl (C$_1$–C$_4$)/amino alkyl (C$_2$–C$_4$) esters of acrylic and methacrylic acids such as N,N-diethylaminoethyl acrylate, N-t-butylaminopropyl acrylate, N,N-dimethylaminoethyl methacrylate, N-t-butylaminoethyl methacrylate, and the quaternization product of dimethylaminoethyl methacrylate and dimethyl sulfate, diethyl sulfate and the like; diacetone acrulamide; and vinyl esters such as vinyl acetate and vinyl propionate; styrene and alkyl-substituted monomers such as styrene and alpha-methyl styrene; C$_1$–C$_8$ dialkyl maleates; N-vinyl pyrrolidone; and N-substituted alkyl (C$_1$–C$_8$ maleamic acids.

The polymerization is initiated by a free radical initiator such as peracid or salt thereof, e.g., hydrogen peroxide, sodium peroxide, lithium peroxide, peracetic acid, persulfuric acid or the ammonium and alkali metal salts thereof, e.g. ammonium persulfate, sodium peracetate, lithium persulfate, potassium persulfate, sodium persulfate, t-butyl peracetate, etc. Various azo compounds may also be used, azobisisobutyronitrile, for example. A suitable concentration of the initiator is from 0.05 to 10 weight percent and preferably from 0.1 to 3 weight percent.

The free radical initiator can be used alone and thermally decomposed to release the free radical initiating species or can be used in combination with a suitable reducing agent in a redox couple. The reducing agent is typically an oxidizable sulfur compound such as an alkali metal metabisulfite and pyrosulfite, e.g. sodium metabisulfite.

If emulsion polymerization procedures are employed, the emulsifying agent is generally any of the nonionic oil-in-water surface active agents or mixtures thereof generally employed in emulsion polymerization procedures. When combinations of emulsifying agents are used, it is advantageous to use a relatively hydrophobic emulsifying agent in combination with a relatively hydrophilic agent. The amount of emulsifying agent is generally from about 1 to about 10, preferably from about 2 to about 8, weight percent of the monomers used in the polymerization.

The emulsifier used in the polymerization can also be added, in its entirety, to the initial charge or a portion of the emulsifier, e.g. from 90 to 25 percent thereof, can be added continuously or intermittently during polymerization.

The preferred interpolymerization procedure is a modified batch process wherein the major amounts of some or all the comonomers and emulsifier are charged to the reaction vessel after polymerization has been initiated. In this manner, control over the copolymerization of monomers having widely varied degrees of reactivity can be achieved. It is preferred to add a small portion of the monomer emulsion initially and then the remainder of the monomer emulsion intermittently or continuously over the polymerization period which can be from 0.5 to about 10 hours, preferably from about 1 to about 5 hours.

The resulting polymeric emulsion or solution contains 10 to 80%, preferably about 30 to 60% solids, by weight. It may be used directly or the polymer may be recovered in solid form or spray-dried.

An alternative method for the production of the betaine polymer involves first the polymerization of the tertiary amine monomer with subsequent quarternization of the polymer with phosphonomethylamine reagent. More specifically, these polymers are synthesized by first polymerizing a monomer of the general structure

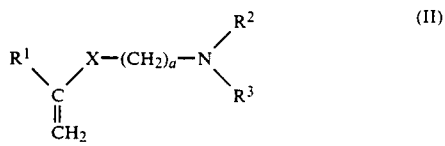

(II)

where R$^1$, X, a, R$^2$, and R$^3$ are as defined above to give a homopolymer or, if other ethylenically unsaturated comonomers are used, a copolymer. The resultant polymers can be represented by the general structure:

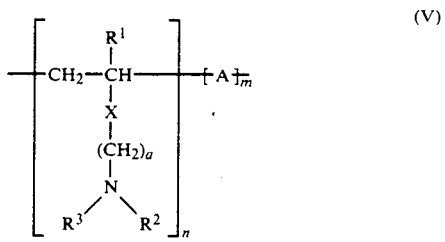

(V)

where $R^1$, X, a, $R^2$, and $R^3$ are as previously defined, n and m are positive integers, and A is a repeating unit derived from one or more ethylenically unsaturated comonomers. These polymers are then reacted with a compound of general structure

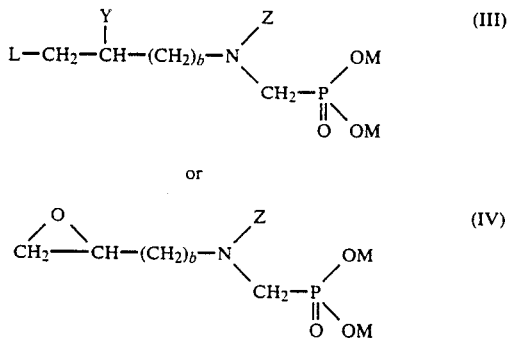

under conditions analogous to those previously described for the monomer preparation.

The resulting derivatized polymers can be represented by the general structure

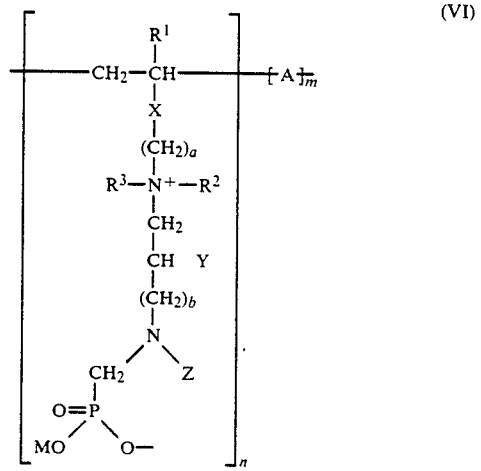

where $R^1$, X, a, $R^2$, $R^3$, Y, b, Z, M, n, A, and m are as previously defined. In the latter case, the reagents, reaction conditions and isolation procedures for the quaternization are substantially the same as those described previously however the yields are in the range of about 50 to 70% conversion.

The copolymers are generally used in their neutralized form as produced above. However they may be further neutralized with appropriate neutralizing agent; the only other essential ingredients in hair spray formulations are the solvent and the propellant. While in some cases, particularly with chlorofluorocarbons, the propellant can be used as the solvent also, it is anticipated that the materials of this invention will be primarily used with non-halogenated solvents and hydrocarbon propellants. In these formulations, the solvents of choice are alcohols, particularly the low boiling, more volatile alcohols.

In general, $C_1$-$C_4$ straight and branched-chain alcohols can be used, with ethanol, propanol, and isopropanol being the preferred solvents. In addition to their excellent solubilizing properties, these solvents are quite volatile (and, thus, evaporate quickly) and are compatible with containers ordinarily used for pressurized aerosols.

While the polymers used in these formulations are compatible with virtually any of the aerosol propellants known to those skilled in the art including halocarbons such as trichlorofluoromethane, it is preferred to use non-halogenated hydrocarbons as the propellants to avoid the release of halocarbons into the atmosphere. Preferred propellants are the lower boiling hydrocarbons, preferably $C_3$-$C_6$ straight and branched chain hydrocarbons, more preferably propane, butane, isobutane and mixtures thereof. Other propellants suitable for use in these formulations include ethers such as dimethyl ether.

If further neutralization is utilized, many alkaline neutralizing agents may be employed including NaOH, KOH, and mixtures of NaOH and/or KOH with long chain amines such as those described in U.S. Pat. No. 4,192,861 issued Mar. 11, 1980, to Micchelli et al., and incorporated herein by reference. However, the preferred neutralizing agents are organic amines, preferably 2-amino-2-methyl-1-propanol (AMP) and 2-amino-2-methyl-1,3-propanediol (AMPD), more preferably AMP. These agents, which are widely used in the hair spray industry, produce neutralized copolymers having good hydrocarbon tolerance and shampoo removability.

In general, the method for preparing the hair fixative formulations of this invention involves dissolving or diluting the copolymer in the selected solvent(s), adding the neutralizing agent if present, and subsequently adding any optional compounds whose presence may be desired, and combining the resultant solution with the selected aerosol propellant.

It should be noted that the novel hair fixative formulations of this invention will, in all cases, contain at least three, and sometimes four, essential components. The first and second of these components are the active ingredients which comprise one or more of the above-described copolymers, which serve as the fixative for the formulation, and an appropriate neutralizing agent (if utilized) as described above. The third component comprises one or more solvents which serve as vehicles for the binder. The last component is the propellant which serves to effect the discharge of the aforedescribed fixative and vehicle from the container wherein the formulation was packaged. Water is not ordinarily present, but may be included in some formulations, as may other optional ingredients.

With regard to proportions, the final hair spray formulations typically contain the neutralized copolymeric fixative in a concentration ranging from about 0.5 to 9%, by weight,; the solvent in a concentration ranging from about 10 to 90%, by weight; and, the propellant concentration ranging from 10 to 85%, by weight, wherein all percentages total 100%. These proportions should, however, be considered as being merely illustrative inasmuch as it may well be desirable to prepare operable formulations having concentrations of components which fall outside the above suggested ranges for particular applications.

As stated above, optional additives may also be incorporated into the hair fixing formulations of this invention in order to modify certain properties thereof. Among these additives may be included; plasticizers such as glycols, phthalate esters and glycerine; silicones; emollients, lubricants and penetrants such as lanolin compounds; protein hydrolyzates and other protein derivatives; ethylene oxide adducts, and polyoxyethylene cholesterol; U.V. absorbers; dyes and other colorants; and, perfumes. The copolymeric binders of this invention show little or no tendency to chemically interact with such additives.

The resulting hair fixing formulations exhibit all of the characteristics required of such a product. Their films are transparent, glossy, flexible and strong. They possess good antistatic properties, adhere well to hair, are easily removed by soapy water or shampoos. Further, when on the hair the films allow the hair to be readily recombed, do not yellow on aging, do not become tacky when exposed to high humidities, and have excellent curl retention under high humidity conditions.

EXAMPLE 1

This example illustrates the preparation of haloalkylaminoalkylmethylenephosphonic acids from N-haloalkyl-N-alkyl amines, formaldehyde, and phosphorous acid. These compounds correspond to FIG. III where L is chlorine, Y is hydrogen and Z is methyl. These compounds were made according to the procedure of K. Moedritzer and R R. Irani, J. Org, Chem 31 1603 (1966).

A 2 liter flask was equipped with a mechanical stirrer, thermometer, condenser heating mantle, and addition funnel. Phosphorous acid (148.4 g, 1.80 mol), N-(2-chloroethyl) N-methylamine hydrochloride (235.0 g, 1.80 mol), and water (260 ml) were charged to the flask. Concentrated hydrochloric acid (240 ml) was added slowly. The reaction mixture was heated to reflux and formalin solution (292.8 g, 37% solution, 3.60 mol) was added over 1 hour. After the addition was complete, the reaction mixture was held at reflux an additional 2 hours. The reaction mixture was then cooled to room temperature.

The reaction mixture was subsequently concentrated on a rotary evaporator to give a thick syrup. Water (250 ml) was added and the solution was again evaporated (to remove as much excess HCl as possible). This procedure was repeated several times. Finally, the thick syrup was dissolved in SDA-40 alcohol (250 g) to give an ethanolic product solution weighing 647.3 g and containing 1.93 meg ionic Cl/g and 2.63 meg organic Cl/g.

EXAMPLE 2

This example illustrates the preparation of alpha-aminomethylenephosphonate betaines from reaction of N-dialkylaminoalkyl acrylamides or 2-substituted acrylamides with haloalkylaminoalkylmethylenephosphonic acids from Example 1. This compound corresponds to Formula I where Y is H, Z is —$CH_3$, b is 0, $R_1$, $R_2$, and $R_3$ are —$CH_3$, X is CONH, and a is 3.

A 3-L 4-necked flask was equipped with a mechanical stirrer, thermometer, condenser, addition funnel, and heating mantle dimethylaminopropylmethacrylamide (279.9 g, 1.645 mol) and methyl ether hydroquinone (MEHQ) (0.28 g) were charged to the reactor. The phosphonic acid from Example 1 (635.0 g solution, 1.645 mol) was then added over ½ hour. The reaction mixture was then warmed to 55° C. and a solution of KOH (162.7 g, 2.90 mol) in SDA-40 alcohol (880 g) was added over 1 hour. The reaction mixture was held at 55° for an additional 3 hours, then cooled to room temperature.

The precipitated KCl was filtered on a Buchner funnel. The filtrate containing the phosphonate betaine monomer gave the following analyses: weight 1176.0 g; ionic Cl 0.3597 meg/g; unsaturation 1.21 meg/.g. This solution contained the desired phosphonate betaine monomer at a concentration of 43.1% W/W.

EXAMPLE 3

This example illustrates the copolymerization of the phosphonate betaine monomer obtained in Example 2 with representative methacrylate esters in SDA-40 alcohol to give polymeric products useful in hair fixative formulations. In the table, all parts are listed by weight. Vazo 67 is 2-methyl, 2,2'-azobisbutanenitrile from Du Pont Chemical Corp.

| Material | Example 3A | Example 3B | Example 3C | |
|---|---|---|---|---|
| Vazo 67 | 0.825 | 0.825 | 0.825 | Initial Charge |
| DMAPMA | 24.75 | 88.70 | 88.70 | |
| Phosphonate Betaine | 516.8 | 197.3 | 197.3 | |
| n-Butyl methacrylate | 82.7 | 236.5 | 236.5 | Slow-added 1 |
| Methyl methacrylate | 164.8 | — | — | |
| Lauryl methacrylate | — | 85.0 | — | |
| Stearyl methacrylate | — | — | 85.0 | |
| SDA-40 alcohol | — | 181.5 | 181.5 | |
| SDA-40 alcohol | 40.0 | 40.0 | 40.0 | Slow-add 2 |
| Vazo 67 | 5.0 | 5.0 | 5.0 | |
| SDA-40 alcohol | 330.0 | 330.0 | 330.0 | Dilution |
| SDA-40 alcohol | 35.0 | 35.0 | 35.0 | Slow-add 3 |
| Vazo 67 | 9.9 | 9.9 | 9.9 | |

Three 2 liter 4-necked flasks were equipped with thermometers, hot water baths, mechanical stirrers, condensers, and addition funnels. The initial charge and 15% by volume of slow-add 1 was charged to the flasks. The flask contents were then heated to reflux. After refluxing for 10 minutes, the remainder of slow-add 1 was added over 1½ hours. Starting at the same time, slow-add 2 was added over 4 hours. The polymerization mixture was held in reflux an additional 3 hours. During the hold period the dilution is added uniformly in order to control viscosity.

When the hold period is complete, slow-add 3 is added over a ½ hour. The polymerization mixture is held in reflux for an additional 4 hours and then cooled to room temperature. The polymer solutions were filtered through a celite pad on a Buchner funnel in order to remove precipitated KCl (carried into the polymerization via the phosphonate betaine monomer from Example 2).

| Analysis | Example 3A | Example 3B | Example 3C |
|---|---|---|---|
| % solids | 26.0 | 27.7 | 31.2 |
| ionic chloride $\left(\frac{meq}{g\ dry}\right)$ | 0.384 | 0.205 | 0.184 |
| I.V. (1% in SDA-40) | 0.240 | 0.197 | 0.221 |
| Residual BMA (ppm as is) | 126 | 446 | 645 |
| Residual LMA (ppm as is) | — | 284 | — |
| Residual SMA (ppm as is) | — | — | <1000 |
| Brookfield viscosity (cps) | 320 | 68 | 111 |
| Calc'd % KCl (dry basis) | 2.87 | 1.53 | 1.40 |
| Theoretical acidity $\left(\frac{meq}{g\ dry}\right)$ | 1.21 | 0.45 | 0.45 |
| Observed acidity $\left(\frac{meq\ H^+}{g\ dry}\right)$ | 1.10 | 0.46 | 0.45 |
| Theoretical % N (dry) | 6.37 | 5.21 | 5.21 |
| Observed % N (dry) | 5.49 | 5.73 | 5.25 |

EXAMPLE 4

This example illustrates the preparation of a carboxylate betaine monomer and the copolymerization of this monomer with representative methacrylate esters in SDA-40 alcohol. The resulting carboxylate betaine copolymers were used as control examples for comparison with the phosphonate betaine copolymers from Example 3.

Carboxylate Betaine Monomer

A 3-L 4-necked flask was equipped with a mechanical stirrer, thermometer, condenser, addition funnel, and heating mantle. Dimethylaminopropyl methacrylamide (398.7 g, 2.344 mol), SDA-40 alcohol (220 ml) and MEHQ (0.4 g) were charged to the flask. The reactor contents were warmed to 55° C. Ethyl chloroacetate (239.7 g, 1.956 mol) was added uniformly over 1 hour. The reaction mixture was held at 55° C. until gas chromatagraphic analysis for ethyl chloroacetate indicated the reaction to be complete. A solution of KOH (109.8 g, 1.956 mol) in SDA-40 alcohol (450 ml) was then added uniformly over 1½ hours. The reaction mixture was held at 55° C. for 3 hours then cooled to room temperature. The solution was filtered free of precipitated KCl and concentrated to a total weight of 567.8 g. The monomer solution contained (as determined by bromine titration and potentiometric titration) 67.4 wt. % carboxylate betaine and 6.8 wt. % DMAPMA.

The polymerizations of the above monomer were carried out in the same manner as the polymerizations described in Example 3. In all cases, the monomers were used in equivalent molar quantities for comparison with the phosphonate betaine copolymers of Example 3. The weights and materials used are tabulated below:

| Material | Example 4A | Example 4B | Example 4C | |
|---|---|---|---|---|
| Vazo | 0.825 | 0.825 | 0.825 | Initial Charge |
| DMAPMA | 10.4 | 83.2 | 83.2 | Slow-add 1 |
| Carboxylate betaine monomer | 210.8 | 80.4 | 80.4 | |
| N-butyl methacrylate | 82.7 | 236.5 | 236.5 | |
| Methyl methacrylate | 164.8 | — | — | |
| Lauryl methacrylate | — | 85.0 | — | |
| Stearyl methacrylate | — | — | 85.0 | |
| SDA-40 | 180.0 | 212.0 | 212.0 | |
| SDA-40 | 40.0 | 40.0 | 40.0 | Slow-add 2 |
| Vazo 67 | 5.0 | 5.0 | 5.0 | |
| SDA-40 | 330. | 330. | 330. | Dilution |
| SDA-40 | 35.0 | 35.0 | 35.0 | Slow-add 3 |
| Vazo 67 | 9.9 | 9.9 | 9.9 | |
| % solids | 38.3 | 42.8 | 42.8 | |
| ionic chloride $\left(\frac{meq}{g\ dry}\right)$ | 0.188 | 0.072 | 0.075 | |
| I.V. (1% in SDA-40) | 0.39 | 0.23 | 0.20 | |
| Residual BMA (ppm as is) | 69 | 268 | 369 | |
| Residual MMA (ppm as is) | 798 | — | — | |
| Residual LMA (ppm as is) | — | 317 | — | |
| Residual SMA (ppm as is) | — | — | <1000 | |
| Brookfield viscosity (cps) | 68,600 | 1150 | 1075 | |

HYDROCARBON TOLERANCE

To assess the maximum quantity of hydrocarbon which can be tolerated in an aerosol formulation by the polymer mixtures, the polymer samples were formulated as 2% (by weight) solids using anhydrous ethanol as the solvent and A-46 propellant, a hydrocarbon propellant comprising approximately 80% (by weight) isobutane and 20% (by weight) propane. Any residual acidity was fully neutralized with AMP. The propellant was then added to the desired proportion and the formulations, in clear glass tubes, were chilled to −10° C. The maximum amount of propellant tolerated (i.e., that above which phase separation, as evidenced by the onset of turbidity, occurred) at this temperature was observed. The results are presented in Table I:

TABLE I

| Polymer Sample No. | Max. Amount of A46 (in weight %) Tolerated |
|---|---|
| 3A | 40 |
| 3B | 60 |
| 3C | 60 |
| 4A | 25 |
| 4B | 65 |
| 4C | 65 |

The percentage curl retention was calculated as follows:

$$\text{Curl Retention \%} = \frac{L - L_t}{L - L_o} \times 100$$

Where:
$L$ length of hair fully extended
$L_o$ length of hair before exposure
$L_t$ length of hair after exposure

TABLE II

| Sample/Time (Hrs) | 0.25 | 0.50 | 1.00 | 1.50 | 2.00 | 3.00 | 4.00 | 5.00 | 24.00 |
|---|---|---|---|---|---|---|---|---|---|
| 3A | 96.8 | 96.8 | 94.8 | 94.8 | 94.8 | 94.8 | 94.8 | 94.8 | 94.1 |
| 3B | 96.8 | 92.8 | 92.0 | 91.4 | 90.0 | 90.0 | 90.0 | 88.7 | 83.3 |
| 3C | 93.1 | 91.7 | 90.5 | 89.8 | 87.9 | 87.1 | 85.8 | 85.8 | 82.4 |
| 4A | 96.1 | 94.8 | 94.1 | 93.3 | 93.3 | 93.3 | 93.3 | 93.3 | 89.7 |
| 4B | 94.1 | 93.4 | 92.1 | 90.7 | 90.7 | 89.4 | 89.4 | 87.4 | 85.3 |
| 4C | 96.3 | 93.7 | 93.7 | 91.2 | 89.3 | 89.3 | 87.4 | 86.7 | 85.5 |

The above data demonstrates, particularly in the comparison of Samples 3A and 4A, the advantages achieved by the use of the phosphonate betaines of the present invention. Comparisons of samples 3B and 3C with 4B and 4C do not show a pronounced improvement in this testing due to the inherent hydrocarbon tolerance of the base polymer imparted by the presence of the long chain methacrylate esters in the copolymers.

SHAMPOO REMOVABILITY

To assess the shampoo removability of the hair spray formulations of this invention, a series of 4% solutions of the copolymers produced in Example 3 and 4 in anhydrous ethanol were prepared.

These formulations were each sprayed on 8 swatches of 10" Brown European Virgin hair, a total of 20 times (10 times each on the front and back); after a ½ hour air-drying period, the spraying was repeated and the swatches were air-dried for an additional hour. Immediately thereafter each swatch was wetted with warm water, squeezed-dry, and washed for 30 seconds with three drops of Prell shampoo. The swatches were then rinsed for 30 seconds, squeezed dry, and oven-dried at 120° F. Each sample was then evaluated for stiffness, flake and feel.

Using the above procedure, the hair spray formulations prepared with the phosphonate betaines (of Example 3A) were found to have significantly less stiffness and flake and softer feel, all indicative of better shampoo removability, than the corresponding carboxylated betaine 4A. Due to the inherent poor shampoo removability due to the presence of the long chain methacrylate functionality in the B and C samples, no significant differences were observed using this subjective evaluation technique. However, it is to be noted that if lower levels of the long chain esters were present in the polymers of Examples 3B and 3C, the advantages of the phosphonate over the corresponding carboxylate would be apparent in the resulting hair spray formulations.

CURL RETENTION

High humidity curl retention tests were also performed, comparing the phosphonated and carboxylated betaines. The test conditions were 72° F., 90% relative humity for 24 hours. The average retention of nine curls at each time interval is shown in Table II.

In summary, the test results presented above show that by using the phosphonate betaine copolymers in hair fixatives, there is no negative impact on the curl retention while achieving improvements in hydrocarbon tolerance and shampoo removability over many of the hair care formulations of the prior art.

Now that preferred embodiments of the present invention have been described in detail, various modifications and improvements thereon will become readily apparent to those skilled in the art. Accordingly, the spirit and scope of the present invention is to be limited only by the appended claims, and not by the foregoing disclosure.

We claim:

1. A hair fixative composition comprising a solvent and a hydrocarbon propellant and a functional amount of an alpha-aminomethylenephosphonphonate betaine copolymer prepared from at least 5% of a betaine monomer of the formula:

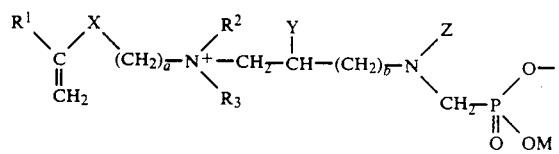

where
$R^1$ is hydrogen or methyl;
X is

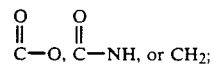

a is 0, 1, 2, or 3, with the condition that when X is

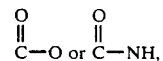

that a be greater than 1;
$R^2$ and $R^3$ are independently $C_1$-$C_6$ alkyl, aryl, benzyl, or cyclohexyl;
Y is hydrogen or hydroxyl;
b is 0, 1, 2, or 3;
Z is $C_1$-$C_6$ alkyl, aryl, benzyl, cyclohexyl, or $$CH_2-P\overset{O}{\underset{OM}{\overset{\|}{/}}}\overset{OM}{\underset{}{\backslash}}$$

and

M is hydrogen, metallic cation, or ammonium ion; and up to 95% by weight of an ethylenically unsaturated copolymerizable comonomer.

2. The hair fixative of claim 1 wherein $R^1$, $R^2$ and $R^3$ are methyl, X is C—NH; and Z is methyl.

3. The hair fixative of claim 1 wherein the ethylenically unsaturated comonomer is selected from the group consisting of acrylic or methacrylic acids and esters thereof with $C_1$-$C_{18}$ alcohols; unsaturated carboxylic acids and esters thereof; (meth)acrylamide and their N-substituted derivatives; vinyl esters; vinyl ethers; N-vinyl lactams; halogenated vinyl compounds; alkyl vinyl ketones; diesters; and polyethyleneglycol or polypropyleneglycol acrylate or methacrylate.

4. The hair fixative of claim 3 wherein the comonomer is acrylic or methacrylic acid or an ester thereof.

5. The hair fixative of claim 4 wherein the comonomer is acrylic acid.

6. The hair fixative of claim 1 wherein the ethylenically unsaturated comonomer is present in an amount greater than 50% by weight.

7. The hair fixative of claim 1 wherein there is additionally present up to about 20% (by weight) of one or more comonomers selected from the group consisting of acrylic and methacrylic esters of hydroxyalkyl esters of acrylic and methacrylic acids, $C_1$-$C_4$ alkyl/$C_2$-$C_4$ amino alkyl esters of acrylic and methacrylic acids, styrene and alkyl substituted styrene monomers, vinyl esters, $C_1$-$C_8$ dialkyl maleates, N-vinyl pyrrolidone, and N-substituted alkyl ($C_1$-$C_8$) maleamic acid.

8. The hair fixative composition of claim 1 wherein the betaine copolymer is further neutralized with an alkaline neutralizing agent.

9. The hair fixative of claim 8 wherein the alkaline neutralizing agent is selected from the group consisting of 2-amino-2-methyl-1-propanol, 2-amino-2-methyl-1,3-propanediol, potassium hydroxide or sodium hydroxide.

10. A hair spray formulation comprising a hair fixative composition comprising a solvent and a hydrocarbon propellant and a functional amount of an alpha-aminomethylenephosphonate betaine copolymer prepared from at least 5% of a betaine monomer of the formula.

$$R^1\diagdown_{\underset{CH_2}{\overset{\|}{C}}}\diagup^X-(CH_2)_a-\overset{R^2}{\underset{R_3}{\overset{|}{N^+}}}-CH_2-\overset{Y}{\underset{|}{CH}}-(CH_2)_b-N\diagup^Z\diagdown_{CH_2-P\overset{O}{\underset{O}{\overset{\|}{\diagdown}}}\diagup^{O-}_{OM}}$$

where
$R^1$ is hydrogen or methyl;
X is $$\overset{O}{\overset{\|}{C}}-O,\ \overset{O}{\overset{\|}{C}}-NH,\ or\ CH_2;$$

a is 0, 1, 2, or 3, with the condition that when X is $$\overset{O}{\overset{\|}{C}}-O\ or\ \overset{O}{\overset{\|}{C}}-NH,$$

that a be greater than 1;
$R^2$ and $R^3$ are independently $C_1$-$C_6$ alkyl, aryl, benzyl, or cyclohexyl;
Y is hydrogen or hydroxyl;
b is 0, 1, 2, or 3;
Z is $C_1$-$C_6$ alkyl, aryl, benzyl, cyclohexyl, or $$CH_2-P\overset{O}{\underset{OM}{\overset{\|}{/}}}\overset{OM}{\underset{}{\backslash}}$$

and

M is hydrogen, metallic cation, or ammonium ion; and up to 95% by weight of an ethylenically unsaturated copolymerizable comonomer.

11. The formulation of claim 10, wherein the solvent is a $C_1$-$C_4$ straight or branched chain alcohol.

12. The formulation of claim 10, wherein the hydrocarbon propellant is selected from group consisting of $C_3$-$C_6$ straight chain hydrocarbons, $C_4$-$C_6$ branched chain hydrocarbons, and mixtures thereof.

13. The formulation of claim 10, wherein the hair fixative composition further comprises about 2.5 to about 20% (by weight) of one or more comonomers selected from the group consisting of acrylic and methacrylic esters of hydroxyalkyl esters of acrylic and methacrylic acids, $C_1$-$C_4$ alkyl/$C_2$-$C_4$ amino alkyl esters of acrylic and methacrylic acids, styrene and alkyl substituted styrene monomers, vinyl esters, $C_1$-$C_8$ dialkyl maleates, N-vinyl pyrrolidone, and N-substituted alkyl ($C_1$-$C_8$) maleamic acid.

14. The formulation of claim 10 wherein $R^1$, $R^2$ and $R^3$ are methyl, X is C—NH; and Z is methyl.

* * * * *